(12) United States Patent
Pradeep et al.

(10) Patent No.: US 8,386,312 B2
(45) Date of Patent: *Feb. 26, 2013

(54) NEURO-INFORMATICS REPOSITORY SYSTEM

(75) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/113,863

(22) Filed: May 1, 2008

(65) Prior Publication Data

US 2009/0030930 A1 Jan. 29, 2009

Related U.S. Application Data

(60) Provisional application No. 60/915,161, filed on May 1, 2007.

(51) Int. Cl.
*G06Q 30/00* (2012.01)
(52) U.S. Cl. .................. 705/14.42; 705/14.52
(58) Field of Classification Search ............. 705/14.41, 705/14.66
See application file for complete search history.

(56) References Cited

U.S. PATENT DOCUMENTS

| | | | |
|---|---|---|---|
| 2,549,836 A | 4/1951 | McIntyre et al. | |
| 3,490,439 A | 1/1970 | Rolston | |
| 3,572,322 A | 3/1971 | Wade | |
| 3,735,753 A | 5/1973 | Pisarski | |
| 3,880,144 A | 4/1975 | Coursin et al. | |
| 3,901,215 A | 8/1975 | John | |
| 3,998,213 A | 12/1976 | Price | |
| 4,075,657 A | 2/1978 | Weinblatt | |
| 4,149,716 A | 4/1979 | Scudder | |
| 4,201,224 A | 5/1980 | John | |
| 4,279,258 A | 7/1981 | John | |
| 4,411,273 A | 10/1983 | John | |
| 4,417,592 A | 11/1983 | John | |
| 4,537,198 A | 8/1985 | Corbett | |
| 4,557,270 A | 12/1985 | John | |
| 4,610,259 A | 9/1986 | Cohen et al. | |
| 4,613,951 A | 9/1986 | Chu | |

(Continued)

FOREIGN PATENT DOCUMENTS

| GB | 1374658 | 11/1974 |
|---|---|---|
| GB | 2221759 | 2/1990 |

(Continued)

OTHER PUBLICATIONS

Sutherland, Max, "Neuromarketing: What's It All About?" From Max Sutherland's Weblog at www.sutherlandsurvey.com, Feb. 2007, p. 1-5.

(Continued)

*Primary Examiner* — Ella Colbert
*Assistant Examiner* — Scott S Trotter
(74) *Attorney, Agent, or Firm* — Hanley, Flight & Zimmerman, LLC

(57) ABSTRACT

A neuro-informatics repository system is provided to allow efficient generation, management, and access to central nervous system, autonomic nervous system, effector data, and behavioral data obtained from subjects exposed to stimulus material. Data collected using multiple modalities such as Electroencephalography (EEG), Electrooculography (EOG), Galvanic Skin Response (GSR), Event Related Potential (ERP), surveys, etc., is stored using a variety of data models to allow efficient querying, report generation, analysis and/or visualization.

26 Claims, 6 Drawing Sheets

| Subject Attributes Queries 315 | | | |
|---|---|---|---|
| Location 317 | Demographic Attributes 319 | Session Information 321 | ... |

| Experimental Design Queries 325 | | | | |
|---|---|---|---|---|
| Experiment Protocols 327 | Product Category 329 | Surveys Included 331 | Stimulus Used 333 | ... |

| Response Assessment Queries 337 | | | | |
|---|---|---|---|---|
| Attention Score 339 | Emotion Score 341 | Retention Score 343 | Effectiveness Score 345 | ... |

U.S. PATENT DOCUMENTS

| | | | |
|---|---|---|---|
| 4,632,122 A | 12/1986 | Johansson et al. | |
| 4,683,892 A | 8/1987 | Johansson et al. | |
| 4,695,879 A | 9/1987 | Weinblatt | |
| 4,736,751 A | 4/1988 | Gevins et al. | |
| 4,800,888 A | 1/1989 | Itil et al. | |
| 4,802,484 A | 2/1989 | Friedman et al. | |
| 4,846,190 A | 7/1989 | John | |
| 4,885,687 A | 12/1989 | Carey | |
| 4,894,777 A | 1/1990 | Negishi et al. | |
| 4,913,160 A | 4/1990 | John | |
| 4,955,388 A | 9/1990 | Silberstein | |
| 4,967,038 A | 10/1990 | Gevins et al. | |
| 4,987,903 A | 1/1991 | Keppel et al. | |
| 5,003,986 A | 4/1991 | Finitzo et al. | |
| 5,038,782 A | 8/1991 | Gevins et al. | |
| 5,052,401 A | 10/1991 | Sherwin | |
| 5,083,571 A | 1/1992 | Prichep | |
| RE34,015 E | 8/1992 | Duffy | |
| 5,137,027 A | 8/1992 | Rosenfeld | |
| 5,213,338 A | 5/1993 | Brotz | |
| 5,226,177 A | 7/1993 | Nickerson | |
| 5,243,517 A * | 9/1993 | Schmidt et al. | 600/544 |
| 5,273,037 A | 12/1993 | Itil et al. | |
| 5,291,888 A | 3/1994 | Tucker | |
| 5,293,867 A | 3/1994 | Oommen | |
| 5,295,491 A | 3/1994 | Gevins | |
| 5,339,826 A | 8/1994 | Schmidt et al. | |
| 5,357,957 A | 10/1994 | Itil et al. | |
| 5,363,858 A | 11/1994 | Farwell | |
| 5,392,788 A | 2/1995 | Hudspeth | |
| 5,406,956 A | 4/1995 | Farwell | |
| 5,447,166 A | 9/1995 | Gevins | |
| 5,474,082 A | 12/1995 | Junker | |
| 5,479,934 A | 1/1996 | Imran | |
| 5,518,007 A | 5/1996 | Becker | |
| 5,537,618 A | 7/1996 | Boulton et al. | |
| 5,617,855 A | 4/1997 | Waletzky et al. | |
| 5,655,534 A | 8/1997 | Ilmoniemi | |
| 5,676,138 A | 10/1997 | Zawilinski | |
| 5,720,619 A | 2/1998 | Fisslinger | |
| 5,724,987 A | 3/1998 | Gevins et al. | |
| 5,729,205 A | 3/1998 | Kwon | |
| 5,740,035 A | 4/1998 | Cohen et al. | |
| 5,762,611 A | 6/1998 | Lewis et al. | |
| 5,771,897 A | 6/1998 | Zufrin | |
| 5,787,187 A | 7/1998 | Bouchard et al. | |
| 5,800,351 A | 9/1998 | Mann | |
| 5,812,642 A | 9/1998 | Leroy | |
| 5,817,029 A | 10/1998 | Gevins et al. | |
| 5,848,399 A | 12/1998 | Burke | |
| 5,945,863 A | 8/1999 | Coy | |
| 5,961,332 A * | 10/1999 | Joao | 434/236 |
| 5,983,129 A | 11/1999 | Cowan et al. | |
| 6,001,065 A | 12/1999 | DeVito | |
| 6,021,346 A | 2/2000 | Ryu et al. | |
| 6,052,619 A | 4/2000 | John | |
| 6,099,319 A * | 8/2000 | Zaltman et al. | 434/236 |
| 6,120,440 A * | 9/2000 | Goknar | 600/300 |
| 6,128,521 A | 10/2000 | Marro et al. | |
| 6,154,669 A | 11/2000 | Hunter et al. | |
| 6,161,030 A | 12/2000 | Levendowski et al. | |
| 6,173,260 B1 | 1/2001 | Slaney | |
| 6,175,753 B1 | 1/2001 | Menkes et al. | |
| 6,228,038 B1 | 5/2001 | Claessens | |
| 6,236,885 B1 | 5/2001 | Hunter et al. | |
| 6,254,536 B1 | 7/2001 | DeVito | |
| 6,280,198 B1 * | 8/2001 | Calhoun et al. | 434/236 |
| 6,286,005 B1 | 9/2001 | Cannon | |
| 6,289,234 B1 | 9/2001 | Mueller | |
| 6,292,688 B1 | 9/2001 | Patton | |
| 6,301,493 B1 | 10/2001 | Marro et al. | |
| 6,315,569 B1 | 11/2001 | Zaltman | |
| 6,330,470 B1 | 12/2001 | Tucker et al. | |
| 6,334,778 B1 * | 1/2002 | Brown | 434/258 |
| 6,374,143 B1 | 4/2002 | Berrang et al. | |
| 6,381,481 B1 | 4/2002 | Levendowski et al. | |
| 6,398,643 B1 | 6/2002 | Knowles et al. | |
| 6,422,999 B1 | 7/2002 | Hill | |
| 6,434,419 B1 | 8/2002 | Gevins et al. | |
| 6,453,194 B1 | 9/2002 | Hill | |
| 6,487,444 B2 | 11/2002 | Mimura | |
| 6,488,617 B1 | 12/2002 | Katz | |
| 6,510,340 B1 | 1/2003 | Jordan | |
| 6,520,905 B1 | 2/2003 | Surve et al. | |
| 6,545,685 B1 | 4/2003 | Dorbie | |
| 6,575,902 B1 | 6/2003 | Burton | |
| 6,577,329 B1 | 6/2003 | Flickner et al. | |
| 6,585,521 B1 | 7/2003 | Obrador | |
| 6,594,521 B2 | 7/2003 | Tucker | |
| 6,598,006 B1 | 7/2003 | Honda et al. | |
| 6,654,626 B2 | 11/2003 | Devlin et al. | |
| 6,662,052 B1 | 12/2003 | Sarwal et al. | |
| 6,665,560 B2 | 12/2003 | Becker et al. | |
| 6,688,890 B2 | 2/2004 | von Buegner | |
| 6,708,051 B1 | 3/2004 | Durousseau | |
| 6,712,468 B1 | 3/2004 | Edwards | |
| 6,754,524 B2 | 6/2004 | Johnson, Jr. | |
| 6,757,556 B2 | 6/2004 | Gopinathan et al. | |
| 6,788,882 B1 | 9/2004 | Geer et al. | |
| 6,792,304 B1 | 9/2004 | Silberstein | |
| 6,842,877 B2 * | 1/2005 | Robarts et al. | 715/708 |
| 6,904,408 B1 | 6/2005 | McCarthy et al. | |
| 6,950,698 B2 | 9/2005 | Sarkela et al. | |
| 6,958,710 B2 | 10/2005 | Zhang et al. | |
| 6,973,342 B1 | 12/2005 | Swanson | |
| 6,993,380 B1 | 1/2006 | Modarres | |
| 7,130,673 B2 | 10/2006 | Tolvanen-Laakso et al. | |
| 7,150,715 B2 | 12/2006 | Collura et al. | |
| 7,164,967 B2 | 1/2007 | Etienne-Cummings et al. | |
| 7,177,675 B2 | 2/2007 | Suffin et al. | |
| 7,222,071 B2 | 5/2007 | Neuhauser et al. | |
| 7,272,982 B2 | 9/2007 | Neuhauser et al. | |
| 7,286,871 B2 | 10/2007 | Cohen | |
| 7,340,060 B2 | 3/2008 | Tomkins et al. | |
| 7,391,835 B1 | 6/2008 | Gross et al. | |
| 7,408,460 B2 | 8/2008 | Crystal et al. | |
| 7,420,464 B2 | 9/2008 | Fitzgerald et al. | |
| 7,443,292 B2 | 10/2008 | Jensen et al. | |
| 7,460,827 B2 | 12/2008 | Schuster et al. | |
| 7,463,143 B2 | 12/2008 | Forr et al. | |
| 7,463,144 B2 | 12/2008 | Crystal et al. | |
| 7,471,987 B2 | 12/2008 | Crystal et al. | |
| 7,483,835 B2 | 1/2009 | Neuhauser et al. | |
| 7,496,400 B2 | 2/2009 | Hoskonen et al. | |
| 7,548,774 B2 | 6/2009 | Kurtz et al. | |
| 7,551,952 B2 | 6/2009 | Gevins et al. | |
| 7,592,908 B2 | 9/2009 | Zhang et al. | |
| 7,623,823 B2 | 11/2009 | Zito et al. | |
| 7,636,456 B2 | 12/2009 | Collins et al. | |
| 7,650,793 B2 | 1/2010 | Jensen et al. | |
| 7,689,272 B2 | 3/2010 | Farwell | |
| 7,697,979 B2 | 4/2010 | Martinerie et al. | |
| 7,698,238 B2 | 4/2010 | Barletta et al. | |
| 7,720,351 B2 | 5/2010 | Levitan | |
| 7,729,755 B2 | 6/2010 | Laken | |
| 7,809,420 B2 | 10/2010 | Hannula et al. | |
| 7,840,248 B2 | 11/2010 | Fuchs et al. | |
| 7,840,250 B2 | 11/2010 | Tucker | |
| 7,865,394 B1 | 1/2011 | Calloway | |
| 7,892,764 B2 | 2/2011 | Xiong et al. | |
| 7,908,133 B2 | 3/2011 | Neuhauser | |
| 7,917,366 B1 | 3/2011 | Levanon et al. | |
| 7,962,315 B2 | 6/2011 | Jensen et al. | |
| 7,988,557 B2 | 8/2011 | Soderland | |
| 8,014,847 B2 * | 9/2011 | Shastri et al. | 600/410 |
| 8,098,152 B2 | 1/2012 | Zhang et al. | |
| 8,135,606 B2 | 3/2012 | Dupree | |
| 8,209,224 B2 | 6/2012 | Pradeep et al. | |
| 8,229,469 B2 | 7/2012 | Zhang et al. | |
| 8,270,814 B2 | 9/2012 | Pradeep et al. | |
| 2001/0020236 A1 | 9/2001 | Cannon | |
| 2001/0056225 A1 | 12/2001 | DeVito | |
| 2002/0065826 A1 | 5/2002 | Bell et al. | |
| 2002/0072952 A1 | 6/2002 | Hamzey et al. | |
| 2002/0077534 A1 | 6/2002 | DuRousseau | |
| 2002/0155878 A1 | 10/2002 | Lert, Jr. et al. | |
| 2002/0156842 A1 | 10/2002 | Signes et al. | |

| Publication No. | Date | Inventor |
|---|---|---|
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1* | 1/2003 | Gevins et al. ............... 600/544 |
| 2003/0036955 A1 | 2/2003 | Tanaka et al. |
| 2003/0059750 A1* | 3/2003 | Bindler et al. ............... 434/236 |
| 2003/0073921 A1 | 4/2003 | Sohmer et al. |
| 2003/0100998 A2 | 5/2003 | Brunner et al. |
| 2003/0104865 A1 | 6/2003 | Itkis et al. |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0187167 A1 | 9/2004 | Maguire et al. |
| 2004/0210159 A1* | 10/2004 | Kibar ............... 600/558 |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0223237 A1 | 10/2005 | Barletta et al. |
| 2005/0227233 A1* | 10/2005 | Buxton et al. ............... 435/6 |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0035707 A1 | 2/2006 | Nguyen et al. |
| 2006/0053110 A1 | 3/2006 | McDonald et al. |
| 2006/0093998 A1 | 5/2006 | Vertegaal |
| 2006/0111644 A1 | 5/2006 | Guttag et al. |
| 2006/0129458 A1 | 6/2006 | Maggio |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0293921 A1 | 12/2006 | McCarthy et al. |
| 2007/0048707 A1 | 3/2007 | Caamano et al. |
| 2007/0055169 A1 | 3/2007 | Lee et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0078706 A1 | 4/2007 | Datta et al. |
| 2007/0079331 A1 | 4/2007 | Datta et al. |
| 2007/0106170 A1 | 5/2007 | Dunseath, Jr. et al. |
| 2007/0135727 A1 | 6/2007 | Virtanen et al. |
| 2007/0135728 A1 | 6/2007 | Snyder et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0081961 A1 | 4/2008 | Westbrook et al. |
| 2008/0082019 A1 | 4/2008 | Ludving et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0152300 A1 | 6/2008 | Knee et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0062629 A1 | 3/2009 | Pradeep et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0112077 A1 | 4/2009 | Nguyen et al. |
| 2009/0253996 A1 | 10/2009 | Lee et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0060300 A1 | 3/2010 | Mueller et al. |
| 2010/0125219 A1 | 5/2010 | Harris et al. |
| 2010/0145215 A1 | 6/2010 | Pradeep et al. |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0257052 A1 | 10/2010 | Zito et al. |
| 2010/0325660 A1 | 12/2010 | Holden |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0208515 A1 | 8/2011 | Neuhauser |
| 2011/0237971 A1 | 9/2011 | Pradeep et al. |
| 2011/0248729 A2 | 10/2011 | Mueller et al. |
| 2011/0270620 A1 | 11/2011 | Pradeep et al. |

| | | | |
|---|---|---|---|
| 2011/0276504 A1 | 11/2011 | Pradeep et al. | |
| 2011/0282231 A1 | 11/2011 | Pradeep et al. | |
| 2011/0282232 A1 | 11/2011 | Pradeep et al. | |
| 2011/0282749 A1 | 11/2011 | Pradeep et al. | |
| 2012/0036004 A1 | 2/2012 | Pradeep et al. | |
| 2012/0036005 A1 | 2/2012 | Pradeep et al. | |
| 2012/0054018 A1 | 3/2012 | Pradeep et al. | |
| 2012/0072289 A1 | 3/2012 | Pradeep et al. | |
| 2012/0108995 A1 | 5/2012 | Pradeep et al. | |
| 2012/0114305 A1 | 5/2012 | Holden | |
| 2012/0245978 A1 | 9/2012 | Crystal et al. | |

FOREIGN PATENT DOCUMENTS

| | | |
|---|---|---|
| WO | 95-18565 | 7/1995 |
| WO | 97/17774 | 5/1997 |
| WO | 97/40745 | 11/1997 |
| WO | 97/41673 | 11/1997 |
| WO | 02-100241 | 12/2002 |
| WO | 02-102238 | 12/2002 |
| WO | 2004/049225 | 6/2004 |
| WO | 2008/121651 | 10/2008 |
| WO | 2008/137579 | 11/2008 |
| WO | 2008/154410 | 12/2008 |
| WO | 2009/018374 | 2/2009 |
| WO | 2009/052833 | 4/2009 |

OTHER PUBLICATIONS

Barcelo, Francisco, et al., "Prefrontal Modulation of Visual Processing in Humans," Nature Neuroscience, vol. 3, No. 4, Apr. 2000, pp. 399-403.
Canolty, R.T., et al., "High Gamma Power Is Phase-Locked to Theta Oscillations in Human Neocortex," Science, vol. 313, Sep. 15, 2006, pp. 1626-1628.
Engel, Andreas, et al., "Dynamic Predictions: Oscillations and Synchrony in Top-Down Processing," Macmillan Magazines Ltd, vol. 2, Oct. 2001, pp. 704-716.
Fries, Pascal, "A Mechanism for Cognitive Dynamics: Neuronal Communication Through Neuronal Coherence," TRENDS in Cognitive Sciences, vol. 9, No. 10, Oct. 2005, p. 474-480.
Gazzaley, Adam, et al., "Top-down Enhancement and Suppression of the Magnitude and Speed of Neural Activity," Journal of Cognitive Neuroscience, vol. 17, No. 3, pp. 507-517.
Hartikainen, Kaisa, et al., "Emotionally Arousing Stimuli Compete with Attention to Left Hemispace," Editorial Manager(tm) for NeuroReport, Manuscipt Draft, Manuscript No. NR-D-07-5935R1, submitted Sep. 8, 2007, 26 pages.
Knight, Robert T., "Contribution of Human Hippocampal Region to Novelty Detection," Nature, vol. 383, Sep. 19, 1996, p. 256-259.
Knight Robert T., "Decreased Response to Novel Stimuli After Prefrontal Lesions in Man," Electroencephalography and Clinical Neurophysiology, vol. 59, 1984, pp. 9-20.
Miltner, Woflgang H.R., et al., "Coherence of Gamma-band EEG Activity as a Basis for Associative Learning," Nature, vol. 397, Feb. 4, 1999, pp. 434-436.
EEG Protocols, Protocols for EEG Recording, Nov. 13, 2007, 3 pages.
Nielsen, Finn Arup, Neuroinformatics in Functional Neuroimaging, Information and Mathematical Modeling Technical University of Denmark, Aug. 30, 2002, 241 pages.
PCT Notification of Transmittal of the International Search Report and the Written Opinion of the International Searching Authority, or the Declaration, Application No. PCT/US 08/62273, 6 pages.
Final Rejection, issued by the United States Patent and Trademark Office in connection with U.S. Appl. No. 12/056,211, on Jul. 8, 2011, 16 pages.
Office Action, issued by the United States Patent and Trademark Office in connection with U.S. Appl. No. 12/056,211, on Jan. 7, 2011, 19 pages.
Office Action issued by the United States Patent and Trademark Office in connection with U.S. Appl. No. 12/056,221, on Apr. 15, 2011, 24 pages.
Final Rejection, issued by the United States Patent and Trademark Office in connection with U.S. Appl. No. 12/113,870, on Apr. 21, 2011, 10 pages.
Office Action, issued by the United States Patent and Trademark Office in connection with U.S. Appl. No. 12/113,870, on Dec. 3, 2010, 12 pages.
Office Action, issued by the United States Patent and Trademark Office in connection with U.S. Appl. No. 12/122,240, on Jun. 10, 2011, 12 pages.
Final Rejection, issued by the United States Patent and Trademark Office in connection with U.S. Appl. No. 12/122,262, on May 26, 2011, 15 pages.
Office Action, issued by the United States Patent and Trademark Office in connection with U.S. Appl. No. 12/122,262, on Dec. 9, 2010, 13 pages.
Final Rejection, issued by the United States Patent and Trademark Office in connection with U.S. Appl. No. 12/135,066, on Jan. 21, 2011, 16 pages.
Office Action, issued by the United States Patent and Trademark Office in connection with U.S. Appl. No. 12/135,066, on Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, on Dec. 23, 2010, 14 pages.
Final Rejection, issued by the United States Patent and Trademark Office in connection with U.S. Appl. No. 12/135,074, on Jun. 9, 2011, 10 pages.
Final Rejection, issued by the United States Patent and Trademark Office in connection with U.S. Appl. No. 12/182,874, on Jul. 7, 2011, 14 pages.
Office Action, issued by the United States Patent and Trademark Office in connection with U.S. Appl. No. 12/182,874, on Dec. 27, 2010, 17 pages.
Office Action, issued by the United States Patent and Trademark Office in connection with U.S. Appl. No. 12/199,557, on Dec. 27, 2010, 14 pages.
Final Rejection, issued by the United States Patent and Trademark Office in connection with U.S. Appl. No. 12/199,557, on Jun. 9, 2011, 12 pages.
Final Rejection, issued by the United States Patent and Trademark Office in connection with U.S. Appl. No. 12/199,583, on Jun. 21, 2011, 14 pages.
Office Action, issued by the United States Patent and Trademark Office in connection with U.S. Appl. No. 12/199,583, on Dec. 27, 2010, 17 pages.
Final Rejection, issued by the United States Patent and Trademark Office in connection with U.S. Appl. No. 12/199,596, on Jun. 14, 2011, 13 pages.
Office Action, issued by the United States Patent and Trademark Office in connection with U.S. Appl. No. 12/199,596, on Dec. 27, 2010, 17 pages.
Final Rejection, issued by the United States Patent and Trademark Office in connection with U.S. Appl. No. 12/200,813, on Jul. 6, 2011, 13 pages.
Office Action, issued by the United States Patent and Trademark Office in connection with U.S. Appl. No. 12/200,813, on Dec. 27, 2010, 14 pages.
Office Action, issued by the United States Patent and Trademark Office in connection with U.S. Appl. No. 12/234,372, on Jun. 7, 2011, 10 pages.
Final Rejection, issued by the United States Patent and Trademark Office in connection with U.S. Appl. No. 12/135,069, on Feb. 17, 2011, 32 pages.
Office Action, issued by the United States Patent and Trademark Office in connection with U.S. Appl. No. 12/135,069, on Oct. 29, 2010, 21 pages.
Office Action, issued by the United States Patent and Trademark Office in connection with U.S. Appl. No. 12/357,315, on May 4, 2011, 9 pages.
Office Action, issued by the United States Patent and Trademark Office in connection with U.S. Appl. No. 12/410,380, on Jun. 7, 2011, 9 pages.

Office Action, issued by the United States Patent and Trademark Office in connection with U.S. Appl. No. 12/413,297, on Jul. 18, 2011, 9 pages.
Office Action, issued by the United States Patent and Trademark Office in connection with U.S. Appl. No. 12/608,685,on Jul. 12, 2011, 15 pages.
Office Action, issued by the United States Patent and Trademark Office in connection with U.S. Appl. No. 12/056,190,on Aug. 10, 2011, 28 pages.
Office Action, issued by the United States Patent and Trademark Office in connection with U.S. Appl. No. 12/357,322,on Aug. 23, 2011, 12 pages.
Office Action, issued by the United States Patent and Trademark Office in connection with U.S. Appl. No. 12/135,069,on Aug. 26, 2011, 33 pages.
Restriction Requirement, issued by the United States Patent and Trademark Office in connection with U.S. Appl. No. 12/122,253,on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
Office Action, issued by the United States Patent and Trademark Office in connection with U.S. Appl. No. 12/135,066, on Sep. 29, 2011, 37 pages.
Restriction Requirement, issued by the United States Patent and Trademark Office in connection with U.S. Appl. No. 12/056,225, on Oct. 3, 2011, 6 pages.
Office Action, issued by the United States Patent and Trademark Office in connection with U.S. Appl. No. 12/234,388, on Oct. 12, 2011, 27 pages.
Office Action, issued by the United States Patent and Trademark Office in connection with U.S. Appl. No. 12/234,372, on Oct. 13, 2011, 22 pages.
Office Action, issued by the United States Patent and Trademark Office in connection with U.S. Appl. No. 12/410,380, on Oct. 19, 2011, 21 pages.
Office Action, issued by the United States Patent and Trademark Office in connection with U.S. Appl. No. 12/357,315, on Oct. 26, 2011, 41 pages.
Office Action, issued by the United States Patent and Trademark Office in connection with U.S. Appl. No. 12/122,240, on Oct. 27, 2011, 39 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.
Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.
International Preliminary Report on Patentability, issued by the International Bureau of WIPO in connection with International Application No. PCT/US08/062275, on Nov. 3, 2009, 1 page.
International Search Report, issued by the International Bureau in connection with International Application No. PCT/US08/062275, on Sep. 22, 2008, 2 pages.
Written Opinion, issued by the International Bureau in connection with International Application No. PCT/US08/062275, on Sep. 22, 2008, 6 pages.
International Preliminary Report on Patentability, issued by the International Bureau of WIPO in connection with International Application No. PCT/US08/063984, on Nov. 17, 2009, 1 page.
International Search Report, issued by the International Bureau in connection with International Application No. PCT/US08/063984, on Sep. 29, 2008, 3 pages.
Written Opinion, issued by the International Bureau in connection with International Application No. PCT/US08/063984, on Sep. 29, 2008, 4 pages.
International Preliminary Report on Patentability, issued by the International Bureau of WIPO in connection with International Application No. PCT/US08/063989, on Nov. 17, 2009, 1 page.
International Search Report, issued by the International Bureau in connection with International Application No. PCT/US08/063989, on Jul. 17, 2008, 2 pages.
Written Opinion, issued by the International Bureau in connection with International Application No. PCT/US08/063989, on Jul. 17, 2008, 4 pages.
International Preliminary Report on Patentability, issued by the International Bureau of WIPO in connection with International Application No. PCT/US08/066166, on Dec. 7, 2009, 1 page.
International Search Report, issued by the International Bureau in connection with International Application No. PCT/US08/066166, on Aug. 25, 2008, 2 pages.
Written Opinion, issued by the International Bureau in connection with International Application No. PCT/US08/066166, on Aug. 25, 2008, 6 pages.
International Preliminary Report on Patentability, issued by the International Bureau of WIPO in connection with International Application No. PCT/US08/071639, on Feb. 2, 2010, 1 page.
International Search Report, issued by the International Bureau in connection with International Application No. PCT/US08/071639, on Oct. 22, 2008, 3 pages.
Written Opinion, issued by the International Bureau in connection with International Application No. PCT/US08/071639, on Oct. 22, 2008, 4 pages.
International Preliminary Report on Patentability, issued by the International Bureau of WIPO in connection with International Application No. PCT/US08/074467, on Mar. 2, 2010, 1 page.
International Search Report, issued by the International Bureau in connection with International Application No. PCT/US08/074467, on Nov. 17, 2008, 2 pages.
Written Opinion, issued by the International Bureau in connection with International Application No. PCT/US08/074467, on Nov. 17, 2008, 4 pages.
International Preliminary Report of Patentability, issued by the International Bureau in connection with International Application No. PCT/US10/021535, on Jul. 26, 2011, 1 page.
International Search Report, issued by the International Bureau in connection with International Application No. PCT/US10/021535, on Mar. 23, 2010, 3 pages.
Written Opinion, issued by the International Bureau in connection with International Application No. PCT/US10/021535, on Mar. 23, 2010, 4 pages.
International Preliminary Report of Patentability, issued by the International Bureau in connection with International Application No. PCT/US09/065368, on Jun. 23, 2011, 2 pages.
International Search Report, issued by the International Bureau in connection with International Application No. PCT/US09/065368, on Jan. 21, 2010, 3 pages.
Written Opinion, issued by the International Bureau in connection with International Application No. PCT/US09/065368, on Jan. 21, 2010, 7 pages.
Extended European Search Report, issued by the European Patent Office in connection with European Application No. 08744383.4-2221/2130146, on Jul. 27, 2011, 6 pages.
Extended European Search Report, issued by the European Patent Office in connection with European Application No. 10173095.0-2221, on Dec. 17, 2010, 3 pages.
Extended European Search Report, issued by the European Patent Office in connection with European Application No. 10189294.1-2221, on Mar. 21, 2011, 7 pages.
First Office Action, issued by the State Intellectual Property Office of P.R. China in connection with Patent Application No. 200880104982.1, on Jan. 25, 2011, 15 pages.
First Office Action, issued by the State Intellectual Property Office of P.R. China in connection with Patent Application No. 2008801015007, on May 25, 2011, 8 pages.

First Office Action, issued by the State Intellectual Property Office of P.R. China in connection with Patent Application No. 200880019166.0, on Jul. 22, 2011, 16 pages.

Decision of Rejection, issued by the State Intellectual Property Office of P.R. China in connection with Patent Application No. 200880104982.1, on Sep. 23, 2011, 10 pages.

Edgar, et al., "Digital Filters in ERP Research," in Event-Related Potentials: A Methods Handbook pp. 85-113, (Todd C. Handy, ed., 2005), 15 pages.

Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Friedman, et al., "Event-Related Potential (ERP) Studies of Memory Encoding and Retrieval: A Selective Review," Microscopy Research and Technique 51:6-26, Wiley-Less, Inc. (2000), 23 pages.

Gaillard, "Problems and Paradigms in ERP Research," Biological Psychology, Elsevier Science Publisher B.V. (1988), 10 pages.

Hopf, et al., "Neural Sources of Focused Attention in Visual Search," Cerebral Cortex, 10:1233-1241, Oxford University Press, (Dec. 2000), 9 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Luck, et al., "The sped of visual attention in schizophrenia: Electrophysiological and behavioral evidence," Schizophrenia Research, pp. 174-195, Elsevier B.V. www.sciencedirect.com, (2006), 22 pages.

Makeig, et al., "Mining event-related brain dynamics," TRENDS in Cognitive Sciences, vol. 8, No. 5, (May 2004), www.sciencedirect.com, 7 pages.

Herrmann, et al., "Mechanisms of human attention: event-related potentials and oscillations," Neuroscience and Biobehavioral Reviews, pp. 465-476, Elsevier Science Ltd., www.elsevier.com/locate/neubiorev, (2001), 12 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal-Hippocampal Habituation to Novel Events," The Journal of Neuroscience, pp. 5356-5363, Society for Neuroscience, (Apr. 29, 2004), 8 pages.

Rugg, et al., "The ERP and cognitive psychology: conceptual issues," (Sep. 1996), 7 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Davidson, et al., "The functional neuroanatomy of emotion and affective style," TRENDS in Cognitive Sciences, vol. 3, No. 1, (Jan. 1999), 11 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Woldorf, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Knight, et al., "Prefrontal cortex regulates inhibition and excitation in distributed neural networks," Acta Psychologica vol. 101, pp. 159-178, Elsevier (1999), 20 pages.

Buschman, et al., "Top-Down versus Bottom-Up Control of Attention in the Prefrontal and posterior Parietal Cortices," Science, vol. 315, www.sciencemag.org/egi/content/full/315/5820/1860, American Association for the Advancement of Science, (2007), 4 pages.

D'Esposito, "From cognitive to neural models of working memory," Phil. Trans. R. Soc. B, doi: 10.1098/rstb.2007.2086, (Mar. 30, 2007), 12 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Hazlett, et al., "Emotional Response to Television Commercials: Facial EMG vs. Self-Report," Journal of Advertising Research, (Apr. 1999), 17 pages.

Makeig, et al., "Dynamic Brain Sources of Visual Evoked Responses," Science, vol. 295, www.sciencemag.org, (Jan. 25, 2002), 5 pages.

Lewis et al., "Market Researchers make Increasing use of Brain Imaging," ACNR, vol. 5, No. 3, pp. 36-37, (Jul./Aug. 2005), 2 pages.

Aaker et al., "Warmth in Advertising: Measurement, Impact, and Sequence Effects," Journal of Consumer Research, vol. 12, No. 4, pp. 365-381, (Mar. 1986), 17 pages.

Belch et al., "Psychophysiological and cognitive Response to Sex in Advertising," Advances in Consumer Research, vol. 9, pp. 424-427, (1982), 6 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Braeutigam, "Neuroeconomics-From neural systems to economic behavior," Brain Research Bulletin, vol. 67, pp. 355-360, Elsevier, (2005), 6 pages.

Lee et al., "What is 'neuromarketing'? A discussion and agenda for future research," International Journal of Psychophysiology, vol. 63, pp. 199-204, Elsevier (2006), 6 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Bagozzi et al., "The Role of Emotions in Marketing," Journal of the Academy of Marketing Science, vol. 27, No. 2, pp. 184-206, Academy of Marketing Science (1999), 23 pages.

Blakeslee, "If You Have a 'Buy Button' in Your Brain, What Pushes It?" The New York Times, www.nytimes.com, (Oct. 19, 2004), 3 pages.

Osborne, "Embedded Watermarking for image Verification in Telemedicine," Thesis submitted for the degree of Doctor of Philosophy, Electrical and Electronic Engineering, University of Adelaide (2005), 219 pages.

Arousal in Sport, in Encyclopedia of Applied Psychology, vol. 1, p. 159, retrieved from Google Books, (Spielberger, ed., Elsevier Academic Press, 2004), 1 page.

Ziegenfuss, "Neuromarketing: Advertising Ethical & Medical Technology," The Brownstone Journal, vol. XII, Boston University, pp. 69-73, (May 2005), 5 pages.

Lekakos, "Personalized Advertising Services Through Hybrid Recommendation Methods: The Case of Digital Interactive Television," Department of Informatics, Cyprus University, (2004), 11 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

U.S. Appl. No. 13/045,457, filed Mar. 10, 2011, (unpublished).
U.S. Appl. No. 12/778,810, filed May 12, 2010, (unpublished).
U.S. Appl. No. 12/778,828, filed May 12, 2010, (unpublished).
U.S. Appl. No. 13/104,821, filed May 10, 2011, (unpublished).
U.S. Appl. No. 13/104,840, filed May 10, 2011, (unpublished).
U.S. Appl. No. 12/853,197, filed Aug. 9, 2010, (unpublished).
U.S. Appl. No. 12/884,034, filed Sep. 16, 2010, (unpublished).
U.S. Appl. No. 12/868,531, filed Aug. 25, 2010, (unpublished).
U.S. Appl. No. 12/913,102, filed Oct. 27, 2010, (unpublished).
U.S. Appl. No. 12/853,213, filed Aug. 9, 2010, (unpublished).
U.S. Appl. No. 13/105,774, filed May 11, 2011, (unpublished).

Klimesch, "EEG alpha and theta oscillations reflect cognitive and memory performanceJul. 20, 2012 a review and analysis," Brain Research Reviews, vol. 29, 169-195, (1999), 27 pages.

Second Office Action, issued by the State Intellectual Property Office of P.R. China in connection with Patent Application No. 200880104982.1, on Jun. 29, 2012, 5 pages.

Final Rejection, issued by the United States Patent and Trademark Office in connection with U.S. Appl. No. 12/056,221, on Nov. 28, 2011, 44 pages.

Office Action, issued by the United States Patent and Trademark Office in connection with U.S. Appl. No. 12/122,262, on Dec. 22, 2011, 17 pages.

Office Action, issued by the United States Patent and Trademark Office in connection with U.S. Appl. No. 12/135,074, on Dec. 22, 2011, 16 pages.

Office Action, issued by the United States Patent and Trademark Office in connection with U.S. Appl. No. 12/199,557, on Dec. 22, 2011, 17 pages.

Office Action, issued by the United States Patent and Trademark Office in connection with U.S. Appl. No. 12/199,596, on Dec. 22, 2011, 15 pages.

Office Action, issued by the United States Patent and Trademark Office in connection with U.S. Appl. No. 12/200,813, on Dec. 22, 2011, 18 pages.

Extended European Search Report, issued by the European Patent Office in connection with European Application No. 11006934.1-2221, on Oct. 25, 2011, 5 pages.

Office Action, issued by the United States Patent and Trademark Office in connection with U.S. Appl. No. 12/199,583, on Dec. 29, 2011, 18 pages.

Final Rejection, issued by the United States Patent and Trademark Office in connection with U.S. Appl. No. 12/410,372, on Jan. 3, 2012, 10 pages.

Final Rejection, issued by the United States Patent and Trademark Office in connection with U.S. Appl. No. 12/413,297, on Jan. 4, 2012, 10 pages.

Office Action, issued by the United States Patent and Trademark Office in connection with U.S. Appl. No. 12/608,660, on Dec. 7, 2011, 43 pages.

Office Action, issued by the United States Patent and Trademark Office in connection with U.S. Appl. No. 12/544,921, on Jan. 9, 2012, 13 pages.

Office Action, issued by the United States Patent and Trademark Office in connection with U.S. Appl. No. 12/357,302, on Jan. 17, 2012, 11 pages.

Office Action, issued by the United States Patent and Trademark Office in connection with U.S. Appl. No. 12/056,225, on Jan. 20, 2012, 12 pages.

Final Rejection, issued by the United States Patent and Trademark Office in connection with U.S. Appl. No. 12/135,066, on Jan. 24, 2012, 12 pages.

Office Action, issued by the United States Patent and Trademark Office in connection with U.S. Appl. No. 12/546,586, on Feb. 1, 2012, 17 pages.

Restriction Requirement, issued by the United States Patent and Trademark Office in connection with U.S. Appl. No. 12/544,958, on Feb. 10, 2012, 6 pages.

Final Rejection, issued by the United States Patent and Trademark Office in connection with U.S. Appl. No. 12/135,069, on Feb. 14, 2012, 35 pages.

Final Rejection, issued by the United States Patent and Trademark Office in connection with U.S. Appl. No. 12/357,322, on Feb. 14, 2012, 14 pages.

Office Action, issued by the United States Patent and Trademark Office in connection with U.S. Appl. No. 12/056,211, on Feb. 16, 2012, 15 pages.

Final Rejection, issued by the United States Patent and Trademark Office in connection with U.S. Appl. No. 12/056,190, on Feb. 17, 2012, 22 pages.

Office Action, issued by the United States Patent and Trademark Office in connection with U.S. Appl. No. 12/122,253, on Feb. 17, 2012, 20 pages.

Office Action, issued by the United States Patent and Trademark Office in connection with U.S. Appl. No. 12/182,874, on Feb. 17, 2012, 15 pages.

First Office Action, issued by the State Intellectual Property Office of P.R. China in connection with Patent Application No. 200880017883.X, on Nov. 30, 2011, 16 pages.

Meriam-Webster Online Dictionary definition for "tangible," available at http://www.meriam-webster.com/dictionary/tangible, 1 page.

Mosby's Dictionary of Medicine, Nursing, & Health Professions, 2009, Mosby, Inc., Definition of Alpha Wave, 1 page.

Mosby's Dictionary of Medicine, Nursing, & Health Professions, 2009, Mosby, Inc., Definition of Beta Wave, 1 page.

U.S. Appl. No. 13/249,512, filed Sep. 30, 2011, (unpublished).
U.S. Appl. No. 13/249,525, filed Sep. 30, 2011, (unpublished).
U.S. Appl. No. 13/288,504, filed Nov. 3, 2011, (unpublished).
U.S. Appl. No. 13/288,571, filed Nov. 3, 2011, (unpublished).
U.S. Appl. No. 12/304,234, filed Nov. 3, 2011, (unpublished).

Office Action, issued by the United States Patent and Trademark Office in connection with U.S. Appl. No. 12/868,531, on Mar. 1, 2012, 6 pages.

Office Action, issued by the United States Patent and Trademark Office in connection with U.S. Appl. No. 12/182,851, on Mar. 12, 2012, 14 pages.

Office Action, issued by the United States Patent and Trademark Office in connection with U.S. Appl. No. 12/608,685, on Mar. 29, 2012, 17 pages.

Office Action, issued by the United States Patent and Trademark Office in connection with U.S. Appl. No. 12/846,242, on Mar. 29, 2012, 15 pages.

Office Action, issued by the United States Patent and Trademark Office in connection with U.S. Appl. No. 12/234,388, on Apr. 6, 2012, 6 pages.

Office Action, issued by the United States Patent and Trademark Office in connection with U.S. Appl. No. 12/357,315, on Apr. 9, 2012, 17 pages.

Office Action, issued by the United States Patent and Trademark Office in connection with U.S. Appl. No. 12/544,958, on May 2, 2012, 14 pages.

English Translation of Office Action, issued by the Israel Patent Office in connection with Patent Application No. 203176, on Feb. 21, 2012, 2 pages.

English Translation of Office Action, issued by the Israel Patent Office in connection with Patent Application No. 203177, on Mar. 1, 2012, 2 pages.

Second Office Action, issued by the State Intellectual Property Office of P.R. China in connection with Patent Application No. 200880101500.7, on Apr. 5, 2012, 5 pages.

Padgett et al., "Categorical Perception in Facial Emotion Classification," In Proceedings of the 18th Annual Conference of the Cognitive Science Society, pp. 249-253 (1996), 5 pages.

de Gelder et al., "Categorical Perception of Facial Expressions: Categories and their Internal Structure," Cognition and Emotion, vol. 11(1), pp. 1-23 (1997), 23 pages.

Bimler et al., "Categorical perception of facial expressions of emotion: Evidence from multidimensional scaling," Cognition and Emotion, vol. 15(5), pp. 633-658 (Sep. 2001), 26 pages.
Newell et al., "Categorical perception of familiar objects," Cognition, vol. 85, Issue 2, pp. 113-143 (Sep. 2002), 31 pages.
Meriam Webster Online Dictionary, Definition of Virtual Reality, available at http://www.meriam-webster.com/dictionary/virtual%20reality, 2 page.
Griss et al., "Characterization of micromachined spiked biopotential electrodes," Biomedical Engineering, IEEE Transactions (Jun. 2002), 8 pages.
"User monitoring," Sapien Systems, available at http://web.archive.org/web/20030818043339/http:/www.sapiensystems.com/eyetracking.html, (Aug. 18, 2003), 1 page.
Sullivan et al., "A brain-machine interface using dry-contact, low-noise EEG sensors," In Proceedings of the 2008 IEEE International Symposium on Circuits and Systems, (May 18, 2008), 4 pages.
Notice of Allowance, issued by the United States Patent and Trademark Office in connection with U.S. Appl. No. 12/357,302, on May 7, 2012, 16 pages.
Notice of Allowance, issued by the United States Patent and Trademark Office in connection with U.S. Appl. No. 12/868,531, on May 8, 2012, 16 pages.
Notice of Allowance, issued by the United States Patent and Trademark Office in connection with U.S. Appl. No. 12/608,696, on May 15, 2012, 16 pages.
Restriction Requirement, issued by the United States Patent and Trademark Office in connection with U.S. Appl. No. 12/545,455, on Jun. 13, 2012, 5 pages.
Office Action, issued by the United States Patent and Trademark Office in connection with U.S. Appl. No. 12/056,225, on Jun. 15, 2012, 9 pages.
Office Action, issued by the United States Patent and Trademark Office in connection with U.S. Appl. No. 12/544,934, on Jun. 18, 2012, 11 pages.
Office Action, issued by the United States Patent and Trademark Office in connection with U.S. Appl. No. 12/135,066, on Jun. 21, 2012, 9 pages.
Final Rejection, issued by the United States Patent and Trademark Office in connection with U.S. Appl. No. 12/608,660, on Jul. 10, 2012, 13 pages.
Second Office Action, issued by the State Intellectual Property Office of P.R. China in connection with Patent Application No. 200880019166.0, on Jun. 5, 2012, 8 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Jung et al., "Analysis and Visualization of Single-Trial Event-Related Potentials," Human Brain Mapping vol. 14, 166-185 (2001), 20 pages.
Krugman, "Brain Wave Measures of Media Involvement," Journal of Advertising Research vol. 11, 3-9 (Feb. 1971), 7 pages.
The Mathworks, Inc., "MATLAB Data Analysis: Version 7," p. 4-19 (2005), 3 pages.
Krakow et al., "Methodology: EEG-correlated fMRI," Functional Imaging in the Epilepsies, (Lippincott Williams & Wilkins, 2000), 17 pages.
Allen et al., "A Method of Removing Imaging Artifact from Continuous EEG Recorded during Functional MRI," Neuroimage, vol. 12, 230-239, (Aug. 2000).
Examinees Answer, issued by the United States Patent and Trademark Office in connection with U.S. Appl. No. 12/234,372, on May 23, 2012, 11 pages.
Advisory Action, issued by the United States Patent and Trademark Office in connection with U.S. Appl. No. 12/234,388, on Aug. 28, 2012, 3 pages.
Examiner's Answer, issued by the United States Patent and Trademark Office in Connection with U.S. Appl. No. 12/410,380, on Jun. 8, 2012, 12 pages.
Examiner's Answer, issued by the United States Patent and Trademark Office in connection with U.S. Appl. No. 12/410,372, on Aug. 3, 2012, 8 pages.
Office Action, issued by the United States Patent and Trademark Office in connection with U.S. Appl. No. 12/545,455, on Aug. 29, 2012, 11 pages.
Final Rejection, issued by the United States Patent and Trademark Office in connection with U.S. Appl. No. 12/608,685, on Jul. 30, 2012, 15 pages.
Office Action, issued by the United States Patent and Trademark Office in connection with U.S. Appl. No. 12/778,810, on Aug. 31, 2012, 12 pages.
Office Action, issued by the United States Patent and Trademark Office in connection with U.S. Appl. No. 12/778,828, on Aug. 30, 2012, 9 pages.
Notice of Allowance, issued by the United States Patent and Trademark Office in connection with U.S. Appl. No. 12/056,190, on Sep. 17, 2012, 11 pages.
Notice of Allowance, issued by the United States Patent and Trademark Office in connection with U.S. Appl. No. 12/122,262, on Sep. 17, 2012, 11 pages.
Final Rejection, issued by the United States Patent and Trademark Office in connection with U.S. Appl. No. 12/122,253, on Sep. 17, 2012, 17 pages.
Examiner's Answer, issued by the United States Patent and Trademark Office in connection with U.S. Appl. No. 12/413,297, on Sep. 18, 2012, 18 pages.
Final Rejection, issued by the United States Patent and Trademark Office in connection with U.S. Appl. No. 12/546,586, on Sep. 18, 2012, 17 pages.
Notice of Allowance, issued by the United States Patent and Trademark Office in connection with U.S. Appl. No. 12/056,211, on Sep. 19, 2012, 10 pages.
Notice of Allowance, issued by the United States Patent and Trademark Office in connection with U.S. Appl. No. 12/135,074, on Sep. 19, 2012, 10 pages.
Notice of Allowance, issued by the United States Patent and Trademark Office in connection with U.S. Appl. No. 12/200,813, on Sep. 20, 2012, 11 pages.
Second Office Action, issued by the State Intellectual Property Office of China in connection with Chinese Patent Application No. 200880017883.X, on Aug. 10, 2012 (9 pages).
Oberman et al., "EEG evidence for mirror neuron activity during the observation of human and robot actions: Toward an analysis of the human qualities of interactive robots," Elsevier, Neurocomputing vol. 70 (2007), Jan. 2, 2007 (10 pages).
U.S. Appl. No. 12/056,190
U.S. Appl. No. 12/056,211
U.S. Appl. No. 12/056,221
U.S. Appl. No. 12/056,225
U.S. Appl. No. 12/113,863
U.S. Appl. No. 12/113,870
U.S. Appl. No. 12/122,240
U.S. Appl. No. 12/122,253
U.S. Appl. No. 12/122,262
U.S. Appl. No. 12/135,066
U.S. Appl. No. 12/135,074
U.S. Appl. No. 12/182,851
U.S. Appl. No. 12/182,874
U.S. Appl. No. 12/199,557
U.S. Appl. No. 12/199,583
U.S. Appl. No. 12/199,596
U.S. Appl. No. 12/200,813
U.S. Appl. No. 12/234,372
U.S. Appl. No. 12/135,069
U.S. Appl. No. 12/234,388
U.S. Appl. No. 12/357,302
U.S. Appl. No. 12/544,921
U.S. Appl. No. 12/544,934
U.S. Appl. No. 12/546,586
U.S. Appl. No. 12/544,958
U.S. Appl. No. 12/410,380
U.S. Appl. No. 12/410,372
U.S. Appl. No. 12/413,297
U.S. Appl. No. 12/545,455
U.S. Appl. No. 12/608,660

U.S. Appl. No. 12/608,685
U.S. Appl. No. 12/608,696
U.S. Appl. No. 12/731,868
U.S. Appl. No. 13/045,457
U.S. Appl. No. 12/778,810
U.S. Appl. No. 12/778,828
U.S. Appl. No. 13/104,821
U.S. Appl. No. 13/104,840
U.S. Appl. No. 12/853,197
U.S. Appl. No. 12/884,034
U.S. Appl. No. 12/868,531
U.S. Appl. No. 12/913,102
U.S. Appl. No. 12/853,213
U.S. Appl. No. 13/105,774
U.S. Appl. No. 12/846,242
U.S. Appl. No. 13/444,149
U.S. Appl. No. 13/569,711
Receipt date: Dec. 07, 2012 12113863 - Gau: 3694 Group B: U.S. App. Serial. No. 12/357,315.
within each application's respective group as identified above. Any relevant/non-cumulative.
/Scott Trotter/ 12/ Dec. 2012.
English Translation of Office Action, issued by the Japanese Patent Office in connection with Patent Application No. 2010-506646, on Oct. 23, 2012, 3 pp.
Notice of Allowance, issued by the United States Patent and Trademark Office in connection with U.S. Appl. No. 12/200,813, on Nov. 2, 2012, 5 pages.
Notice of Allowance, issued by the United States Patent and Trademark Office in connection with U.S. Appl. No. 12/056,190, on Nov. 2, 2012, 5 pages.
Restriction Requirement, issued by the United States Patent and Trademark Office in connection with U.S. Appl. No. 12/056,225, on Nov. 2, 2012, 5 pages.
Final Office Action, issued by the United States Patent and Trademark Office in connection with U.S. Appl. No. 12/135,066, on Nov. 13, 2012, 9 pages.
Notice of Allowance, issued by the United States Patent and Trademark Office in connection with U.S. Appl. No. 12/056,211, on Nov. 21, 2012, 5 pages.
Notice of Allowance, issued by the United States Patent and Trademark Office in connection with U.S. Appl. No. 12/868,531, on Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, on Dec. 10, 2012, 16 pages.
Notice of Allowance, issued by the United States Patent and Trademark Office in connection with U.S. Appl. No. 12/056,190, on Dec. 20, 2012, 5 pages.
Notice of Allowance, issued by the United States Patent and Trademark Office in connection with U.S. Appl. No. 12/056,190, on Dec. 21, 2012, 14 pages.
Notice of Allowance, issued by the United States Patent and Trademark Office in connection with U.S. Appl. No. 12/056,211, on Dec. 21, 2012, 10 pages.
Notice of Allowance, issued by the United States Patent and Trademark Office in connection with U.S. Appl. No. 12/122,262, on Dec. 21, 2012, 19 pages.
Notice of Allowance, issued by the United States Patent and Trademark Office in connection with U.S. Appl. No. 12/135,074, on Dec. 21, 2012, 12 pages.
Notice of Allowance, issued by the United States Patent and Trademark Office in connection with U.S. Appl. No. 12/199,557, on Dec. 21, 2012, 14 pages.
Notice of Allowance, issued by the United States Patent and Trademark Office in connection with U.S. Appl. No. 12/199,596, on Dec. 21, 2012, 17 pages.
Notice of Allowance, issued by the United States Patent and Trademark Office in connection with U.S. Appl. No. 12/200,813, on Dec. 21, 2012, 9 pages.
Notice of Allowance, issued by the United States Patent and Trademark Office in connection with U.S. Appl. No. 12/853,213, on Dec. 21, 2012, 10 pages.
Notice of Allowance, issued by the United States Patent and Trademark Office in connection with U.S. Appl. No. 12/868,531, on Dec. 26, 2012, 2 pages.
Notice of Allowance, issued by the United States Patent and Trademark Office in connection with U.S. Appl. No. 12/199,583, on Dec. 31, 2012, 10 pages.
Final Office Action, issued by the United States Patent and Trademark Office in connection with U.S. Appl. No. 12/182,874, on Jan. 4, 2013, 17 pages.
Notice of Allowance, issued by the United States Patent and Trademark Office in connection with U.S. Appl. No. 12/199,583, on Jan. 11, 2013, 11 pages.
Final Office Action, issued by the United States Patent and Trademark Office in connection with U.S. Appl. No. 12/056,225, on Jan. 11, 2013, 11 pages.
English Translation of Office Action, issued by the Israeli Patent Office in connection with Patent Application No. 201187, on Nov. 27, 2012, 2 pages.
English Translation of Third Office Action, issued by the State Intellectual Property Office of P.R. China in connection with Patent Application No. 200880101500.7, on Nov. 21, 2012, 5 pages.
Extended European Search Report, issued by the European Patent Office in connection with European Application No. 08796890.5-2319/2170161, on Dec. 7, 2012, 9 pages.
Palva et al., "Phase Synchrony Among Neutronal Oscillations in the Human Cortex," Journal of Neuroscience 25 (2005), 3962-3972, 11 pages.
Lachaux et al., "Measuring Phase Synchrony in Brain Signals," Human Brain Mapping 8 (1999), 194-208, 15 pages.

* cited by examiner

| Dataset Data Model 201 | | | | |
|---|---|---|---|---|
| Experiment Name 203 | Client Attributes 205 | Subject Pool 207 | Logistics Information 209 | Stimulus Material 211 |

| Subject Attributes Data Model 215 | | |
|---|---|---|
| Subject Name 217 | Demographic Attributes 219 | Contact Information 221 |

| Neuro-Feedback Association Data Model 225 | | |
|---|---|---|
| Experiment Protocols 227 | Modalities included 229 | Experiment Design Parameters 233 |

| Data Collection Data Model 237 | | | |
|---|---|---|---|
| Recording Attributes 239 | Equipment Attributes 241 | Modalities Recorded 243 | Data Storage Attributes 245 |

| Preset Query Data Model 249 | | | |
|---|---|---|---|
| Query Name 251 | Accessed Data Collection 253 | Access Security Attributes 255 | Refresh Attributes 257 |

Figure 2

| Subject Attributes Queries 315 | | |
|---|---|---|
| Location 317 | Demographic Attributes 319 | Session Information 321 | ... |

| Experimental Design Queries 325 | | |
|---|---|---|
| Experiment Protocols 327 | Product Category 329 | Surveys Included 331 | Stimulus Used 333 | ... |

| Response Assessment Queries 337 | | |
|---|---|---|
| Attention Score 339 | Emotion Score 341 | Retention Score 343 | Effectiveness Score 345 | ... |

Figure 3

| Client Assessment Summary Reports 401 | | |
|---|---|---|
| Effectiveness 403 | Component Assessment 405 | Habituation 407 | ... |

| Client Cumulative Reports 411 | | |
|---|---|---|
| Media Grouped 413 | Campaign Grouped 415 | Time/Location Grouped 417 | ... |

| Industry Cumulative And Syndicated Reports 421 | | | | |
|---|---|---|---|---|
| Aggregate Assessment 423 | Top Performers 425 | Bottom Performers 427 | Outliers 429 | Trend 431 | ... |

Figure 4

NEURO-INFORMATICS REPOSITORY SYSTEM

CROSS REFERENCE TO RELATED APPLICATIONS

This patent claims priority to Provisional Patent Application 60/915,161 titled Neuro-Informatics Repository System, by Anantha Pradeep, Robert T. Knight, and Ramachandran Gurumoorthy, and filed on May 1, 2007. This patent is related to U.S. patent application Ser. No. 12/056,190; U.S. patent application Ser. No. 12/056,211; U.S. patent application Ser. No. 12/056,221; U.S. patent application Ser. No. 12/056,225; U.S. patent application Ser. No. 12/113,870; U.S. patent application Ser. No. 12/122,240; U.S. patent application Ser. No. 12/122,253; U.S. patent application Ser. No. 12/122,262; U.S. patent application Ser. No. 12/135,066; U.S. patent application Ser. No. 12/135,074; U.S. patent application Ser. No. 12/182,851; U.S. patent application Ser. No. 12/182,874; U.S. patent application Ser. No. 12/199,557; U.S. patent application Ser. No. 12/199,583; U.S. patent application Ser. No. 12/199,596; U.S. patent application Ser. No. 12/200,813; U.S. patent application Ser. No. 12/234,372; U.S. patent application Ser. No. 12/135,069; U.S. patent application Ser. No. 12/234,388; U.S. patent application Ser. No. 12/544,921; U.S. patent application Ser. No. 12/544,934; U.S. patent application Ser. No. 12/546,586; U.S. patent application Ser. No. 12/544,958; U.S. patent application Ser. No. 12/846,242; U.S. patent application Ser. No. 12/410,380; U.S. patent application Ser. No. 12/410,372; U.S. patent application Ser. No. 12/413,297; U.S. patent application Ser. No. 12/545,455; U.S. patent application Ser. No. 12/608,660; U.S. patent application Ser. No. 12/608,685; U.S. patent application Ser. No. 13/444,149; U.S. patent application Ser. No. 12/608,696; U.S. patent application Ser. No. 12/731,868; U.S. patent application Ser. No. 13/045,457; U.S. patent application Ser. No. 12/778,810; U.S. patent application Ser. No. 12/778,828; U.S. patent application Ser. No. 13/104,821; U.S. patent application Ser. No. 13/104,840; U.S. patent application Ser. No. 12/853,197; U.S. patent application Ser. No. 12/884,034; U.S. patent application Ser. No. 12/868,531; U.S. patent application Ser. No. 12/913,102; U.S. patent application Ser. No. 12/853,213; and U.S. patent application Ser. No. 13/105,774.

TECHNICAL FIELD

The present disclosure relates to providing a neuro-informatics repository system.

DESCRIPTION OF RELATED ART

Conventional systems for managing neurological and neurophysiological data are limited or nonexistent. In some examples, marketing materials are evaluated using survey based evaluations or neurophysiological measurements taken in isolation. These conventional mechanisms provide some useful data that may be suitable for particular purposes. However, the survey based evaluations or limited neurological measurements used in isolation have limited practical use, particularly when stored inefficiently in existing systems. Furthermore, the survey based evaluations or neurophysiological measurements are highly inefficient and inaccurate due to a variety of semantic, syntactic, metaphorical, cultural, social, and interpretative errors and biases.

Consequently, it is desirable to provide improved methods and apparatus for generating, managing, and accessing a neuro-informatics repository system.

BRIEF DESCRIPTION OF THE DRAWINGS

The disclosure may best be understood by reference to the following description taken in conjunction with the accompanying drawings, which illustrate particular example embodiments.

FIG. 2 illustrates examples of data models that can be used with the neuro-informatics repository system.

FIG. 3 illustrates examples of queries that can be used with the neuro-informatics repository system.

FIG. 4 illustrates examples of reports generated using the neuro-informatics repository system.

DESCRIPTION OF PARTICULAR EMBODIMENTS

Figure 1:
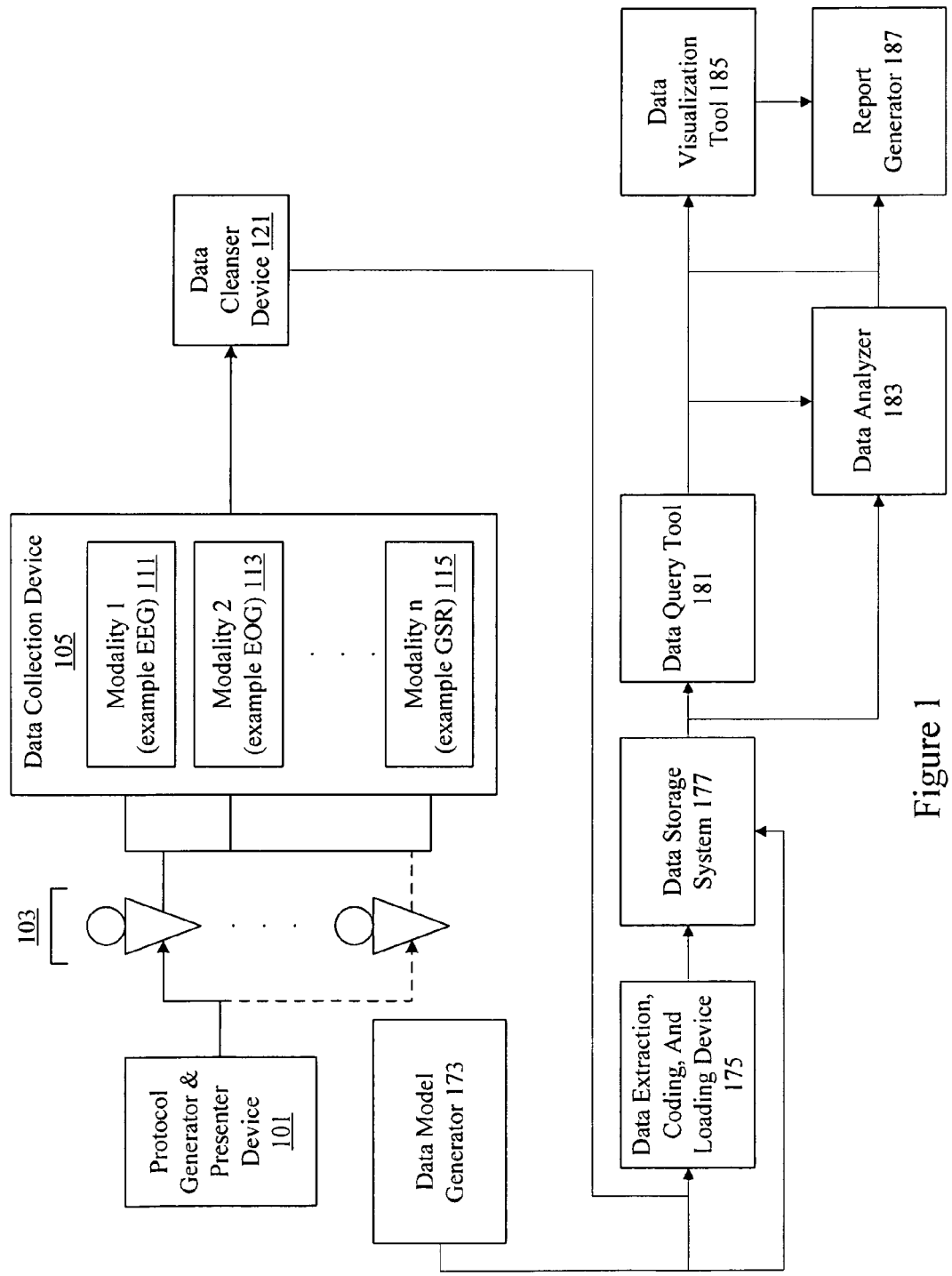
FIG. 1 illustrates one example of a system for implementing a neuro-informatics repository system.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of neurophysiological feedback based assessment of stimuli. However, it should be noted that the techniques and mechanisms of the present invention apply to a variety of different types of data including neuro-physiological, behavioral, and survey based assessments of stimuli including entertainment and marketing such as video and audio streams, media advertising, text, printed advertisements, etc. It should be noted that various mechanisms and techniques can be applied to any type of stimuli. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

A neuro-informatics repository system is provided to allow efficient generation, management, and access to central nervous system, autonomic nervous system, effector data, and behavioral data obtained from subjects exposed to stimulus material. Data collected using multiple modalities such as Electroencephalography (EEG), Electrooculography (EOG), Galvanic Skin Response (GSR), Event Related Potential (ERP), surveys, etc., is stored using a variety of data models to allow efficient querying, report generation, analysis and/or visualization.

Example Embodiments

Conventional mechanisms for obtaining information about subject responses to stimulus materials such as marketing and entertainment materials have generally relied on focus groups and surveys. Subjects are provided with oral and written mechanisms for conveying their thoughts and feelings elicited in response to a particular advertisement, brand, media clip, etc. These oral and written mechanisms provide some limited information on the effectiveness of the marketing and entertainment materials, but have a variety of limitations. For example, subjects may be unable or unwilling to express their true thoughts and feelings about a topic, or questions may be phrased with built in bias. Articulate subjects may be given more weight than nonexpressive ones. A variety of semantic, syntactic, metaphorical, cultural, social and interpretive biases and errors prevent accurate and repeatable evaluation.

The focus groups and survey records could then be filed and stored, but were generally used for only very particular purposes. The ability to generate, manage, and access even these limited focus group and survey records has been lacking. While these conventional mechanisms may be suitable for the particular purpose to which they address, they are not as suitable for providing a repository for the aggregation of neurological and neuro-physiological presentations and assessments of stimulus material including marketing, entertainment, and other audio/visual/tactile/olfactory stimulus across multiple demographics Consequently, the techniques and mechanisms of the present invention obtain neurological and neurophysiological measurements and store the information using a variety of data models. Some examples of central nervous system measurement mechanisms include Functional Magnetic Resonance Imaging (fMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various embodiments, the techniques and mechanisms of the present invention intelligently blend multiple modes and manifestations of precognitive neural signatures with cognitive neural signatures and post cognitive neurophysiological manifestations to more accurately allow assessment of stimulus material. In some examples, autonomic nervous system measures are themselves used to validate central nervous system measures. Effector and behavior responses are blended and combined with other measures. According to various embodiments, central nervous system, autonomic nervous system, and effector system measurements are aggregated into a neuro-feedback significance measurement that is also associated with stimulus material such as a media stream, and stored. This stored information can be used to automatically compress the media stream using an analyzer and visualization tool.

In particular embodiments, neurological and neuro-physiological information is generated and stored using data models to allow efficient querying, report generation and visualization. In some examples, portions of media streams having particular component assessment measures like attention and emotional engagement scores are queried for review. In other examples, industry, category, and client specific percentiles for marketing campaigns may be automatically retrieved for review. In still other examples, location and demographic parameters combined with engagement scores may be used to select materials for visualization or report generation.

A variety of stimulus materials such as entertainment and marketing materials, media streams, billboards, print advertisements, text streams, music, performances, sensory experiences, etc. may be digitized and stored with parameters and neurological and neuro-physiological response data.

According to various embodiments, a neuro-informatics repository system stores neurological and neuro-physiological data generated using a neuro-feedback analyzer that performs both intra-modality measurement enhancements and cross-modality measurement enhancements. According to various embodiments, brain activity is measured not just to determine the regions of activity, but to determine interactions and types of interactions between various regions. The techniques and mechanisms of the present invention recognize that interactions between neural regions support orchestrated and organized behavior. Attention, emotion, memory, and other abilities are not merely based on one part of the brain but instead rely on network interactions between brain regions.

The techniques and mechanisms of the present invention further recognize that different frequency bands used for multi-regional communication can be indicative of the effectiveness of stimuli. In particular embodiments, evaluations are calibrated to each subject and synchronized across subjects. In particular embodiments, templates are created for subjects to create a baseline for measuring pre and post stimulus differentials. According to various embodiments, stimulus generators are intelligent, and adaptively modify specific parameters such as exposure length and duration for each subject being analyzed. An intelligent stimulus generation mechanism intelligently adapts output for particular users and purposes. A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways. Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output that can be stored, managed, and manipulated in a neuro-informatics repository system.

FIG. 1 illustrates one example of a system for using neuro-feedback significance measures determined with central nervous system, autonomic nervous system, and effector measures. According to various embodiments, the neuro-informatics repository system includes a protocol generator and presenter device 101. In particular embodiments, the protocol generator and presenter device 101 is merely a presenter device and merely presents stimulus material to a user. The stimuli may be a media clip, a commercial, pages of text, a brand image, a performance, a magazine advertisement, a movie, an audio presentation, particular tastes, smells, textures and/or sounds. The stimuli can involve a variety of senses and occur with or without human supervision. Continuous and discrete modes are supported. According to various embodiments, the protocol generator and presenter device 101 also has protocol generation capability to allow intelligent customization of stimuli provided to a subject.

According to various embodiments, the subjects are connected to data collection devices 105. The data collection devices 105 may include a variety of neurological and neurophysiological measurement mechanisms such as EEG, EOG, GSR, EKG, pupillary dilation, eye tracking, facial emotion encoding, and reaction time devices, etc. In particular embodiments, the data collection devices 105 include EEG 111, EOG 113, and GSR 115. In some instances, only a single data collection device is used. Data collection may proceed with or without human supervision.

The data collection device 105 collects neuro-physiological data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neurophysiological and neurological data being measured.

In one particular embodiment, the neuro-informatics repository system stores data that includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual. In particular embodiments, the data collection includes behavioral responses and survey responses from individuals.

In particular embodiments, the data collection devices are clock synchronized with a protocol generator and presenter device 101. The data collection system 105 can collect data from a single individual (1 system), or can be modified to collect synchronized data from multiple individuals (N+1 system). The N+1 system may include multiple individuals synchronously tested in isolation or in a group setting. In particular embodiments, the data collection devices also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. In particular embodiments, the data collection devices could be external to the repository system that just provide a source of neuro-physiological and behavioral data to be stored, analyzed, queried, visualized, and reported in the neuro-informatics repository system.

According to various embodiments, the neuro-informatics repository system also includes a data cleanser device 121. In particular embodiments, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject) and endogenous artifacts (where the source could be neurophysiological like muscle movement, eye blinks, etc.). The cleansed data is stored in the neuro-informatics repository storage system.

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser device 121 is implemented using hardware, firmware, and/or software. It should be noted that although a data cleanser device 121 is shown located after a data collection device 105, the data cleanser device 121 like other components may have a location and functionality that varies based on system implementation. For example, some systems may not use any automated data cleanser device whatsoever. In other systems, data cleanser devices may be integrated into individual data collection devices. In other systems, the data cleanser devices could be external to the repository system and provide cleansed data for storage, analysis, and management in the repository system.

According to various embodiments, a data model generator 173 generates and/or enhances the data models used for the storage, querying, analyzing, viewing and reporting of marketing, advertising and other audio/visual/tactile/olfactory stimuli and effectiveness measures or sub-measures. In particular embodiments, the model generator device includes mechanisms to define, modify, and develop data models for recording and describing the attributes of a particular dataset and/or experiment, data models for describing and recording the demography attributes of the subjects included, data models for collating the neuro-physiological and neuro-behavioral assessment mechanism included, data models for collecting the neuro-physiological and neuro-behavioral assessment data and measures, data models for defining and recording pre-set queries into the underlying repository data or data models, data models for generating custom queries into the underlying repository data or data models, data models for specifying data visualizations and data analyses of the underlying data, and data models for the specification of reports to be generated and the formats required The data model generator 173 is connected to a data extraction, coding, and loading device 175. According to various embodiments, the data extraction, coding, and loading device performs extraction of different neuro-physiological and neuro-behavioral response parameters including the original signals, customizes coding of the component and parameters as appropriate to the signals being used, and loads data into the repository system as well as exports data from the repository system.

The mechanisms allow for the identification of response parameters, time-domain and frequency domain evaluation, extraction of relevant information from the signals, and custom transfer of data into and out of the repository system. It should be noted that various components can be implemented using hardware, firmware, and/or software.

According to various embodiments, both the data model generator 173 and the data extraction, coding, and loading device 175 are connected to data storage system 177 that allows custom storage and archival of data with attributes. In particular embodiments, the data storage system 177 uses a database such as a relational, object oriented, or hierarchical database, or a flat file system that allows management and retrieval of neurological, neuro-physiological data, and behavioral data. The physical devices for storage may include tape drives, redundant arrays of independent disks (RAIDs), optical drives, flash memory, or other persistent forms of data storage.

According to various embodiments, the data stored in the data storage system 177 includes the raw data along with metadata and model attributes, as well as other synthesized/morphed forms of the data to allow for efficient access for querying, analysis, export, visualization, and report generation. In particular embodiments, the data also includes the collected neurological and neuro-physiological data from subject responses. The analyzed and synthesized response measures (optionally including the survey responses) could also be stored. In some instances, the stimulus material itself is also stored. The data could be stored internally in a secure, compartmentalized fashion or could be stored in an open or intermingled manner.

A data query tool 181 allows efficient and effective access to data in data storage system 177. According to various embodiments, the data query tool 181 presents preset or custom queries for data in data storage system 177 including queries based on general or customized scripting languages and constructs, visual querying techniques, diagnostic querying including drill-down diagnostics, and scenario queries. The queries execution could be user or system initiated, or could be automated by schedule or could be based on internal/external triggers. The data analyzer 183 can also obtain data from either data storage system 177 or data query tool 181.

According to various embodiments, the data analyzer is a suite of mechanisms provided to analyze the underlying data in the system to identify responses and gain insights. In particular embodiments, neuro-physiological and neuro-behavioral signatures are determined based on time domain analyses and frequency domain analyses. Such analyses use the parameters that are common across the datasets and individuals, as well as parameters that are unique. In particular embodiments, the analyses include statistical parameter extraction and fuzzy logic based attribute estimation from both the time and frequency components of the synthesized response. The statistical parameters used in the blended effectiveness estimates include estimates of skew, peaks, first and second moments of the data, population distribution characteristics, attention, emotional engagement and memory retention. The analyses could also include assessing response measures.

According to various embodiments, the data analyzer 183 may also be associated with an intra-modality response synthesizer and a cross-modality response synthesizer. In particular embodiments, the intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various embodiments, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various embodiments, the data analyzer 183 also includes a composite enhanced effectiveness estimator (CEEE) that combines the enhanced responses and estimates from each modality to provide a blended estimate of the neuro-feedback significance. In particular embodiments, results and measures of the data analyzer are stored in the repository storage system 177.

According to various embodiments, the data visualization tool 185 allows for visualization of the data in multiple ways for different purposes and audiences. In particular embodiments, the visualizations include graphics and/or text. The tool provides options for formats of visualization, samples of visualizations, and mechanisms for implementing combinations of visualization formats. According to various embodiments, the data visualization tool 185 also allows a user to define new visualizations and formats, store and manage generated visualizations, and export the visualizations in one or more formats. In some examples, these visualizations include conversion/compression of the original stimulus for various purposes. In some instances, visualization may include audio or other sensory affects.

A report generator 187 allows for the generation of customized reports in multiple formats using the underling data views, analyzes, insights, and/or visualizations for a variety of purposes and audiences. The report generator 187 supports both preset reports and custom reports and allows a user to specify the data and inferences to be included, the theme of the report, any additional external material for inclusion, and the format required for the report. The reports generation/presentation could be based on pull (user or other system/subsystem initiated) or push (automatic schedules, threshold triggers, etc.) techniques. In some examples, a neuro-informatics repository system is separate from a visualization tool 185 and a report generator 187. For example, a repository system may be server based while a visualization tool 185 and a report generator 187 are remote client.

FIG. 2 illustrates examples of data models that can be used with a neuro-informatics repository system. According to various embodiments, a dataset data model 201 includes an experiment name 203 and/or identifier, client attributes 205, a subject pool 207, logistics information 209 such as the location, date, and time of testing, and stimulus material 211 including stimulus material attributes.

In particular embodiments, a subject attribute data model 215 includes a subject name 217 and/or identifier, contact information 221, and demographic attributes 219 that may be useful for review of neurological and neuro-physiological data. Some examples of pertinent demographic attributes include marriage status, employment status, occupation, household income, household size and composition, ethnicity, geographic location, sex, race. Other fields that may be included in data model 215 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 215 and data models may be preset or custom generated to suit particular purposes.

According to various embodiments, data models for neuro-feedback association 225 identify experimental protocols 227, modalities included 229 such as EEG, EOG, GSR, surveys conducted, and experiment design parameters 233 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 237. According to various embodiments, the data collection data model 237 includes recording attributes 239 such as station and location identifiers, the data and time of recording, and operator details. In particular embodiments, equipment attributes 241 include an amplifier identifier and a sensor identifier.

Modalities recorded 243 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various embodiments, data storage attributes 245 include file storage conventions (format, naming convention, dating convention), storage location, archival attributes, expiry attributes, etc.

A preset query data model 249 includes a query name 251 and/or identifier, an accessed data collection 253 such as data segments involved (models, databases/cubes, tables, etc.), access security attributes 255 included who has what type of access, and refresh attributes 257 such as the expiry of the query, refresh frequency, etc. Other fields such as push-pull preferences can also be included to identify an auto push reporting driver or a user driven report retrieval system.

FIG. 3 illustrates examples of queries that can be performed on a neuro-informatics repository system. According to various embodiments, queries are defined from general or customized scripting languages and constructs, visual mechanisms, a library of preset queries, diagnostic querying including drill-down diagnostics, and eliciting what if scenarios. According to various embodiments, subject attributes queries 315 may be configured to obtain data from a neuro-informatics repository using a location 317 or geographic information, session information 321 such as testing times and dates, and demographic attributes 319. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries may obtain data from a neuro-informatics repository based on experiment protocols 327, product category 329, surveys included 331, and stimulus provided 333. Other fields that may used include the number of protocol repetitions used, combination of protocols used, and usage configuration of surveys.

Client and industry based queries may obtain data based on the types of industries included in testing, specific categories tested, client companies involved, and brands being tested. Response assessment based queries 337 may include attention scores 339, emotion scores, 341, retention scores 343, and effectiveness scores 345. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data from a neuro-informatics repository.

FIG. 4 illustrates examples of reports that can be generated. According to various embodiments, client assessment summary reports 401 include effectiveness measures 403, component assessment measures 405, and habituation measures 407. Effectiveness assessment measures include composite assessment measure(s), industry/category/client specific placement (percentile, ranking, . . . ), actionable grouping assessment such as removing material, modifying segments, or fine tuning specific elements, etc, and the evolution of the effectiveness profile over time. In particular embodiments, component assessment reports include component assessment measures like attention, emotional engagement scores, percentile placement, ranking, etc. Component profile measures include time based evolution of the component measures and profile statistical assessments. According to various embodiments, habituation and wear out reports include the number of times material is assessed, attributes of the multiple presentations used, evolution of the response assessment measures over the multiple presentations, and usage recommendations based on the habituation characteristics.

According to various embodiments, client cumulative reports 411 include media grouped reporting 413 of all stimulus assessed, campaign grouped reporting 415 of stimulus assessed, and time/location grouped reporting 417 of stimulus assessed. According to various embodiments, industry cumulative and syndicated reports 421 include aggregate assessment responses measures 423, top performer lists 425, bottom performer lists 427, outliers 429, and trend r2eporting 431. In particular embodiments, tracking and reporting includes specific products, categories, companies, brands.

A variety of mechanisms can be used to develop and store assessment response measures. In particular embodiments, EEG response data is synthesized to provide an enhanced assessment of neuro-feedback significance. According to various embodiments, EEG measures electrical activity resulting from thousands of simultaneous neural processes associated with different portions of the brain. EEG data can be classified in various bands. According to various embodiments, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and/or magnetoencephalography) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

An information theory based band-weighting model is used for adaptive extraction of selective dataset specific, subject specific, task specific bands to enhance the neuro-informatics repository data. Adaptive extraction may be performed using fuzzy scaling. Stimuli can be presented and enhanced measurements determined multiple times to determine the variation or habituation profiles across multiple presentations. Determining the variation and/or habituation profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Although a variety of synthesis mechanisms are described, it should be recognized that any number of mechanisms can be applied in sequence or in parallel with or without interaction between the mechanisms. In some examples, processes 321 and 327 can be applied to any modality.

Although intra-modality synthesis mechanisms provide enhanced neuro-informatics repository data, additional cross-modality synthesis mechanisms can also be applied to provide enhanced assessment measures. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of significance. However, the techniques of the present invention recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various embodiments, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

Figure 5:
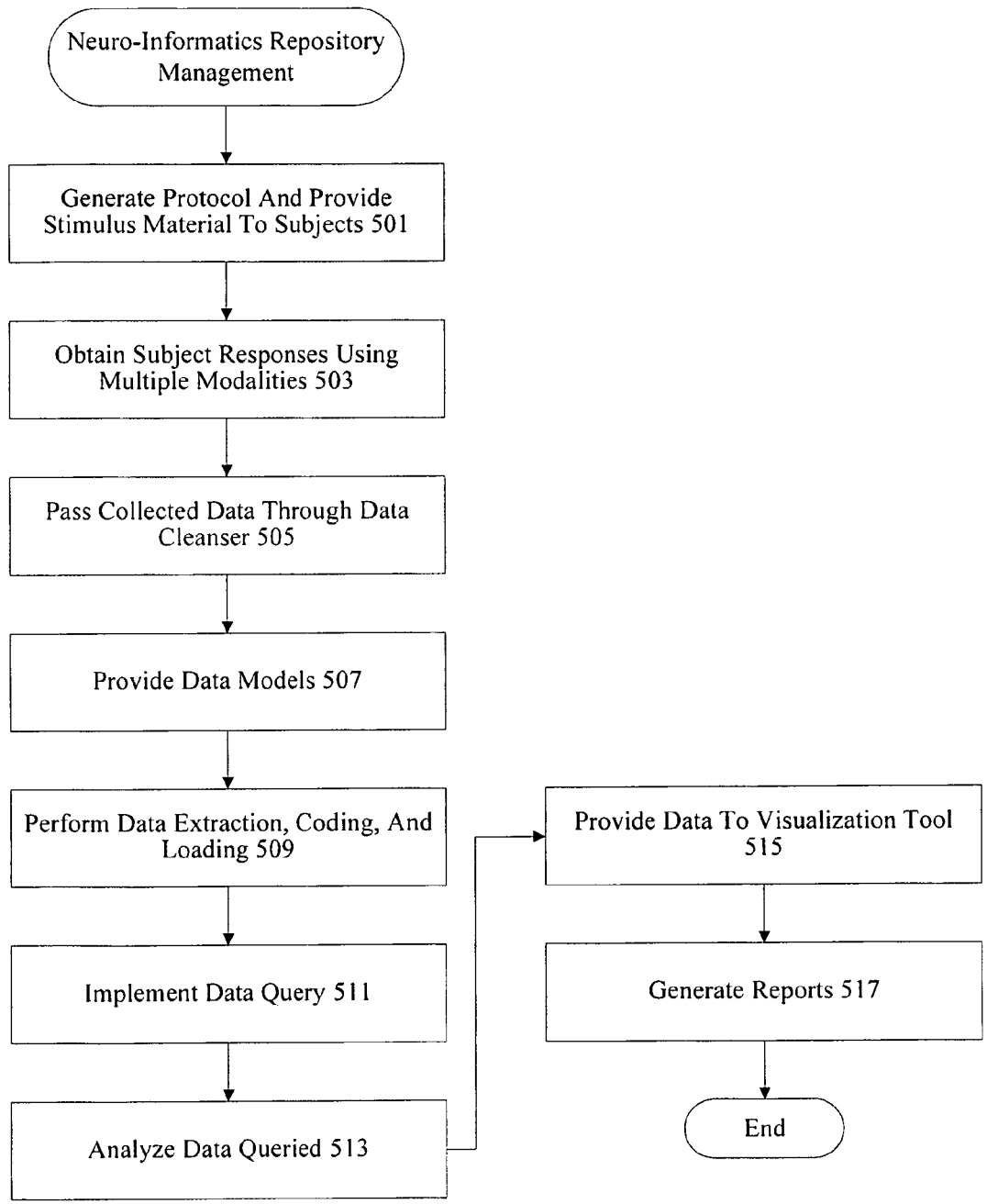
FIG. 5 illustrates one example of a technique for generating, managing, and using a neuro-informatics repository system.

FIG. 5 is a flow process diagram showing a technique for testing, assessing, storing, analyzing, visualizing, and reporting on neurophysiological and behavioral data in a neuroinformatics repository system. At 501, a protocol is generated and stimulus material is provided to one or more subjects. According to various embodiments, stimulus includes streaming video, media clips, printed materials, presentations, performances, games, etc. The protocol determines the parameters surrounding the presentation of stimulus, such as the number of times shown, the duration of the exposure, sequence of exposure, segments of the stimulus to be shown, etc. Subjects may be isolated during exposure or may be presented materials in a group environment with or without supervision. At 503, subject responses are collected using a variety of modalities, such as EEG, ERP, EOG, GSR, etc. In some examples, verbal and written responses can also be collected and correlated with neurological and neurophysiological responses. At 505, data is passed through a data cleanser to remove noise and artifacts that may make data more difficult to interpret. According to various embodiments, the data cleanser removes EEG electrical activity associated with blinking and other endogenous/exogenous artifacts.

At 507, preset and custom data models such as dataset, subject attributes, neuro-feedback association, data collection, and preset query data models are provided. According to various embodiments, data from the data cleanser associated with various data models is provided to perform data extraction, coding, and loading at 509. This allows input of data into a repository system. In particular embodiments, a data query is performed at 511 to extract data from the repository system. According to various embodiments, the queried data is analyzed at 513 for automatic generation of estimates and insights. According to various embodiments, the data is provided to a visualization tool 515 to allow visual presentation in multiple formats. The data is also used to generate reports at 517. In particular embodiments, the system is used in the synthesis of the underlying data to analyze and elicit the marketing or advertising measures being sought for different purposes or audiences.

Figure 6:
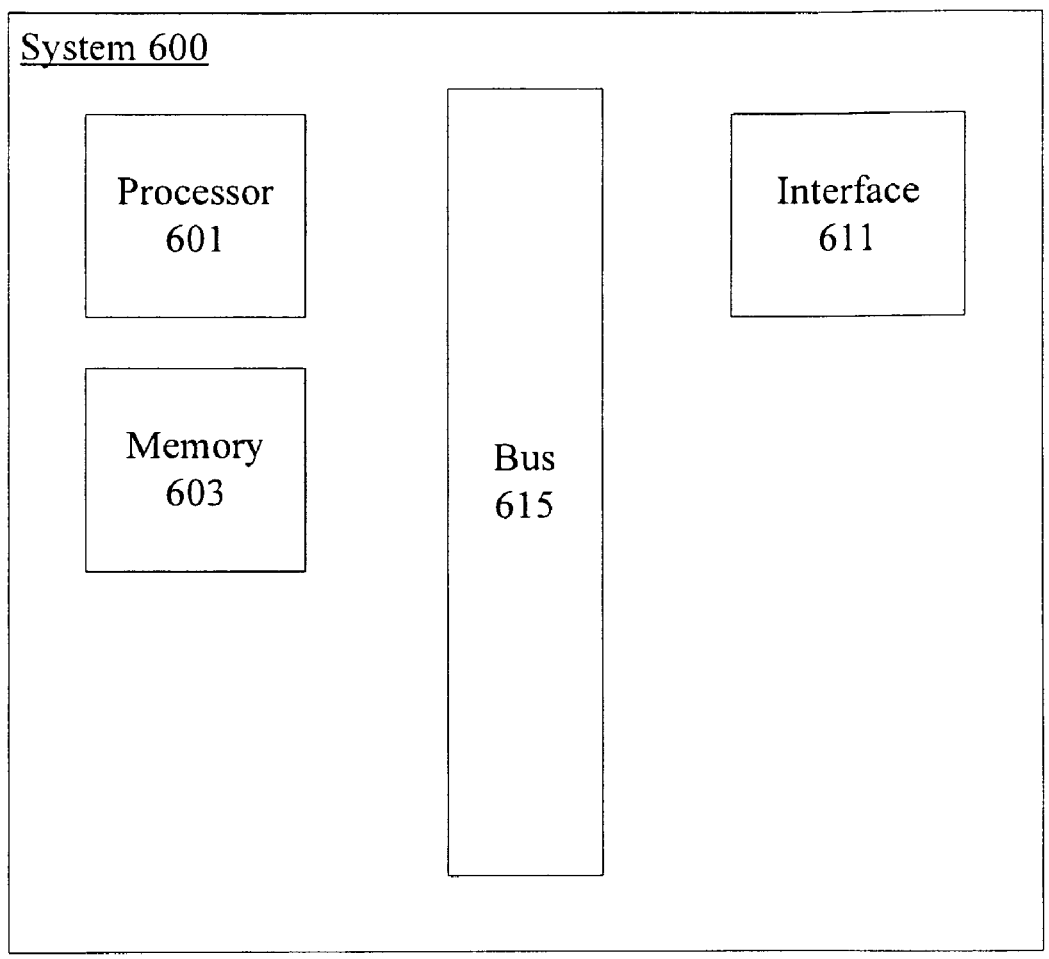
FIG. 6 provides one example of a system that can be used to implement one or more mechanisms.

According to various embodiments, various mechanisms such as the data collection mechanisms, the data analyzer, the report generator, etc. are implemented on multiple devices. However, it is also possible that the various mechanisms be implemented in hardware, firmware, and/or software in a single system. FIG. 6 provides one example of a system that can be used to implement one or more mechanisms. For example, the system shown in FIG. 6 may be used to implement a data cleanser device or a cross-modality responses synthesis device.

According to particular example embodiments, a system 600 suitable for implementing particular embodiments of the present invention includes a processor 601, a memory 603, an interface 611, and a bus 615 (e.g., a PCI bus). When acting under the control of appropriate software or firmware, the processor 601 is responsible for such tasks such as pattern generation. Various specially configured devices can also be used in place of a processor 601 or in addition to processor 601. The complete implementation can also be done in custom hardware. The interface 611 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular example embodiments, the system 600 uses memory 603 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A method, comprising:
analyzing, with a processor, electroencephalography data from a first panelist exposed to a first advertisement or entertainment to determine first effectiveness data for the first advertisement or entertainment, the first effectiveness data being determined based on a degree of asymmetry between a first frequency band of electroencephalography data measured in a first hemisphere of a brain of the first panelist and a second frequency band of the electroencephalography data measured in a second hemisphere of the brain, the degree of asymmetry identified by:
  detecting a first amplitude of the first frequency band;
  detecting a second amplitude of the second frequency band; and
  comparing the first amplitude and the second amplitude to determine a difference between the first amplitude of the first frequency band and the second amplitude of the second frequency band;
assigning the degree of asymmetry to the relationship between the first frequency band and the second frequency band based on the difference between the first amplitude of the first frequency band and the second amplitude of the second frequency band;

generating, with the processor, a data model based on the first effectiveness data, a first emotional engagement based on the asymmetry, a first attribute of the first panelist, and a second attribute of the first advertisement or entertainment;

identifying a third attribute of a second panelist and a fourth attribute of a second advertisement or entertainment corresponding to the first attribute of the first panelist and the second attribute of the first advertisement or entertainment, respectively; and predicting, with the data model, second effectiveness data related to the second panelist and the second advertisement or entertainment.

2. The method of claim 1 further comprising retrieving the encephalography data and at least one of the first or second advertisement or entertainment in response to receipt of a query.

3. The method of claim 1 further comprising retrieving the encephalography data and at least one of the first or third attribute of the first or second panelists in response to receipt of a query.

4. The method of claim 1, wherein the data model further includes data collection information identifying a parameter of a modality of data collection.

5. The method of claim 1, wherein the data model further includes a preset query to obtain data from the data model.

6. The method of claim 1, wherein the data model further includes data related to at least one of an analysis of the encephalography data or a fifth attribute of an experiment.

7. The method of claim 1, further comprising performing intra-modality synthesis to generate the first effectiveness data.

8. The method of claim 1, further comprising:
obtaining second response data from a modality different than electroencephalography; and
performing a cross-modality synthesis on the electroencephalography data and the response data.

9. The method of claim 8, wherein the cross-modality synthesis includes at least one of time shifting or phase shifting at least one of the electroencephalography data or the second response data to align the electroencephalography data with the second response data.

10. The method of claim 8, wherein the modality different than electroencephalography comprises at least one of electrooculography or galvanic skin response.

11. The method of claim 1, wherein at least one of the first or second effectiveness data represents at least one of attention, emotion or memory retention.

12. The method of claim 1 further comprising generating a report based on at least one of the first or second effectiveness data.

13. The method of claim 1, wherein the second frequency band is different than the first frequency band.

14. The method of claim 1, wherein the first panelist comprises a set of first panelists and the second panelist comprises a set of second panelists.

15. A system, comprising:
a data analyzer comprising a processor configured to:
analyze electroencephalography data from a first panelist exposed to a first advertisement or entertainment to determine first effectiveness data for the first advertisement or entertainment, the first effectiveness data being determined based on a degree of asymmetry between a first frequency band of electroencephalography data measured in a first hemisphere of a brain of the panelist and a second frequency band of the electroencephalography data measured in a second hemisphere of the brain, the degree of asymmetry identified by:
detecting a first amplitude of the first frequency band;
detecting a second amplitude of the second frequency band; and
comparing the first amplitude and the second amplitude to determine a difference between the first amplitude of the first frequency band and the second amplitude of the second frequency band; and
assign the degree of asymmetry to the relationship between the first frequency band and the second frequency band based on the difference between the first amplitude of the first frequency band and the second amplitude of the second frequency band; and
a generator to generate a data model based on the first effectiveness data, a first emotional engagement based on the degree of asymmetry, a first attribute of the first panelist, and a second attribute of the first advertisement or entertainment,
the data analyzer to identify a third attribute of a second panelist and a fourth attribute of a second advertisement or entertainment corresponding to the first attribute of the first panelist and the second attribute of the first advertisement or entertainment, respectively, and the data analyzer to predict, with the data model, second effectiveness data related to the second panelist and the second advertisement or entertainment.

16. The system of claim 15 further comprising a data query tool to retrieve the encephalography data and at least one of the first or second advertisement or entertainment in response to receipt of a query.

17. The system of claim 15 further comprising a data query tool to retrieve the encephalography data and at least one of the first or third attribute of the first or second panelists in response to receipt of a query.

18. The system of claim 15, wherein the data model further includes data related to at least one of an analysis of the encephalography data or a fifth attribute of an experiment.

19. The system of claim 15, wherein the data analyzer is to perform intra-modality synthesis with the electroencephalography data to generate the first effectiveness data.

20. The system of claim 15 further comprising a data collector to obtain second response data from a modality different than electroencephalography, the data analyzer to perform cross-modality synthesis on the electroencephalography data and the second response data.

21. The system of claim 20, wherein the modality different than electroencephalography comprises at least one of electrooculography or galvanic skin response.

22. The system of claim 20, wherein the data analyzer is to at least one of time shift or phase shift at least one of the electroencephalography data or the second response data to perform the cross-modality synthesis.

23. The system of claim 15, wherein at least one of the first or second effectiveness data represents at least one of attention, emotion or memory retention.

24. The system of claim 15, wherein the generator is to generate a report based on at least one of the first or second effectiveness data.

25. A tangible machine readable storage device or disc comprising machine readable instructions thereon which, when read, cause a machine to at least:
analyze electroencephalography data from a first panelist exposed to a first advertisement or entertainment to determine first effectiveness data for the first advertisement or entertainment, the first effectiveness data being determined based on a degree of asymmetry between a first frequency band of electroencephalography data measured in a first hemisphere of a brain of the panelist and a second frequency band of the electroencephalography data measured in a second hemisphere of the brain, the degree of asymmetry identified by:
detecting a first amplitude of the first frequency band;
detecting a second amplitude of the second frequency band; and
comparing the first amplitude and the second amplitude to determine a difference between the first amplitude of the first frequency band and the second amplitude of the second frequency band;
assign an asymmetry value to the relationship between the first frequency band and the second frequency band based on the difference between the first amplitude of the first frequency band and the second amplitude of the second frequency band;

generate a data model based on the first effectiveness data, the asymmetry value, a first attribute of the first panelist, and a second attribute of the first advertisement or entertainment;
identify a third attribute of a second panelist and a fourth attribute of a second advertisement or entertainment corresponding to the first attribute of the first panelist and the second attribute of the first advertisement or entertainment, respectively; and
predict, with the data model, second effectiveness data related to the second panelist and the second advertisement or entertainment.

26. The machine readable device or disc of claim 25 further causing the machine to:
generate a report based on at least one of the first or second effectiveness data.

* * * * *